United States Patent
Chan Chun Kong et al.

(10) Patent No.: US 6,936,629 B2
(45) Date of Patent: Aug. 30, 2005

(54) COMPOUNDS AND METHODS FOR THE TREATMENT OR PREVENTION OF FLAVIVIRUS INFECTIONS

(75) Inventors: Laval Chan Chun Kong, Kirkland (CA); Oswy Z. Pereira, Kirkland (CA); Nghe Nguyen-Ba, Laprairie (CA); Thumkunta Jagadeeswar Reddy, St-Laurent (CA); Sanjoy Kumar Das, Laval (CA); Mohammad Arshad Siddiqui, Cambridge, MA (US)

(73) Assignee: ViroChem Pharma Inc., Laval (CA)

( * ) Notice: Subject to any disclaimer, the term of this patent is extended or adjusted under 35 U.S.C. 154(b) by 125 days.

(21) Appl. No.: 10/324,140

(22) Filed: Dec. 20, 2002

(65) Prior Publication Data

US 2003/0199503 A1 Oct. 23, 2003

Related U.S. Application Data

(60) Provisional application No. 60/341,879, filed on Dec. 21, 2001.

(51) Int. Cl.$^7$ ................... A61K 31/426; C07D 277/20
(52) U.S. Cl. ............... 514/370; 548/190; 548/195; 514/365; 514/371; 546/152; 546/270.4; 549/59; 549/429
(58) Field of Search ................ 548/190, 195; 514/371, 365, 370; 546/152, 270.4; 549/59, 429

(56) References Cited

U.S. PATENT DOCUMENTS

| | | | |
|---|---|---|---|
| 3,852,293 | A | 12/1974 | Ariyan et al. |
| 5,284,821 | A | 2/1994 | Ditrich et al. |
| 5,378,680 | A | 1/1995 | Maywald et al. |
| 2002/0099072 | A1 | 7/2002 | Bachand et al. |
| 2003/0032647 | A1 | 2/2003 | Yamada et al. |

FOREIGN PATENT DOCUMENTS

| | | |
|---|---|---|
| EP | 0 419 944 B1 | 4/1991 |
| EP | 0 463 444 B1 | 1/1992 |
| FR | 1.516.777 B1 | 2/1968 |
| WO | WO 00/50424 A1 | 8/2000 |
| WO | WO 01/83460 A1 | 11/2001 |

OTHER PUBLICATIONS

Cook et al., "Studies in the azole series. Part XVII. The preparation and cyclisation reactions of aminocyanoacetamide", Journal of the Chemical Society, 1949, pp. 1440–1442, XP002234179.

Cook et al., "Studies in the azole series. Part I. A novel route to the 5–aminothiazoles", Journal of the Chemical Society, 1947, pp. 1594–1598, XP002234180.

South, M.S., "An unusual labilization of 4–(trifluoromethyl)thiazole", Journal of Heterocyclic Chemistry, vol. 28, No. 4, 1991, pp. 1013–1016, XP002234181.

Bellemin et al., "Synthesis of some pyrazolo '4,3–el '1,21 l–and thiazolo '4,5–e! '1,2! Thiazine 1, 1–dioxide derivatives", Journal of Heterocyclic Chemistry, vol. 21, 1984, pp. 1017–1021, XP002234182.

Robba et al., "Synthése d'intermédiaries de la thiazolo '4,5–d! pyridazine. II. Amides et hydrazides d'acides thiazole–carboxyliques", Bulletin De La Société Chimique De France, No. 6, 1969, pp. 2151–2157, XP002234183.

Coman et al., "Stickstofflost–thiazol–derivate" Archiv Der Pharmazie (Wwinheim), vol. 315, No. 11, 1982, pp. 937–941, XP008014910.

Sekiya et al., "Azole series. I. Reaction of 2–(acylamino)thioacetamides, leading to 5–aminothiazoles and thiazolo '5,4–d! pyrimidines", Chemical and Pharmaceutical Bulletin, vol. 13, No. 11, 1965, pp. 1319–1325. XP008014909.

Smith et al., "Discovery of heterocyclic ureas as a new class of raf kinase inhibitors: identification of a second generation lead by a combinatorial chemistry approach", Bioorganic & Medicinal Chemistry Letters, vol. 11, No. 20, 2001, pp. 2775–2778, XP001118699.

K. Hartke et al., "N–Cyan–thiollmidoester und N,N'–Dicyan–amidine", Archiv Der Pharmazie, 1970, pp. 625–633.

W. Ried et al., "Synthese und Reaktionen neuer Thiazol– und Triazol–Abkömmlinge", Chem. Ber. 116, 1983, pp. 1547–1563.

K. Dridi et al., "Reaction of Mercaptoacetate and Halides Containing Activated Methylenes with Thiocarbamoylimidates: A Novel Approach to the Synthesis of Aminothiazole Derivatives", Synthetic Communications, 28(1), 1998, pp. 167–174.

K. Dridi et al., "Reaction of Mercaptoacetate and Halides Containing Activated Methylenes with Thiocarbamoylimidates: A Novel Approach to the Synthesis of Aminothiazole Derivatives", Synthetic Communications, 29(11), 1999, pp. 2019–2026.

*Primary Examiner*—Golam M M Shameem
(74) *Attorney, Agent, or Firm*—Miller, White, Zdano, Branigan, P.C.

(57) ABSTRACT

The present invention provides novel compounds represented by formula I:

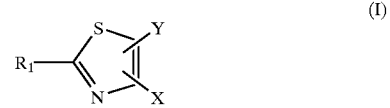

(I)

or pharmaceutically acceptable salts thereof useful for treating flaviviridae viral infection.

78 Claims, No Drawings

COMPOUNDS AND METHODS FOR THE TREATMENT OR PREVENTION OF FLAVIVIRUS INFECTIONS

This application claims the benefit of priority from U.S. Provisional Application 60/341,879, filed Dec. 21, 2001, hereby incorporated by refernce.

FIELD OF THE INVENTION

The present invention relates to novel compounds and a method for the treatment or prevention of Flavivirus infections using novel compounds.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50–60 nm. The HCV genome is a single-stranded, positive-sense RNA of about 9,600 bp coding for a polyprotein of 3009–3030 amino-acids, which is cleaved co and post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different genotypes of HCV respond differently to IFN therapy, genotype 1b is more resistant to IFN therapy than type 2 and 3.

There is therefore a great need for the development of anti-viral agents.

SUMMARY OF THE INVENTION

In accordance with the present invention there is provided a

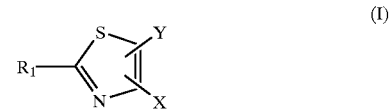

compound having the formula I:
or pharmaceutically acceptable salts thereof,
wherein,
X is chosen from

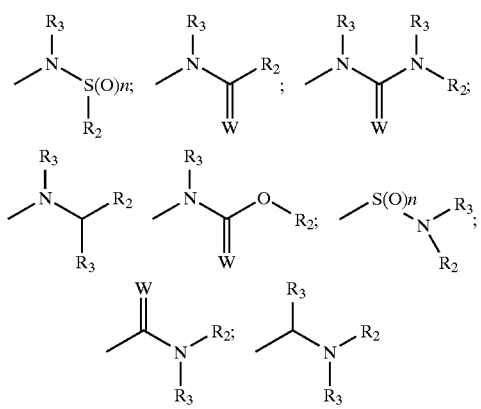

n is an integer between 0 and 2

Y is chosen from $COOR_5$, $COCOOR_5$, $P(O)OR_aOR_b$, $S(O)OR_5$, $S(O)_2OR_5$, an acid bio-isostere, CO-(amino acid), $CONR_cR_d$, $CON(R_4)$—$SO_2$—$R_5$ or $CONR_5OH$, wherein $R_4$, $R_5$, $R_a$, $R_b$, $R_c$ and $R_d$ are each independently chosen from H, $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl;
or $R_a$ and $R_b$ are taken together to form a 5 to 7 membered heterocycle;
or $R_c$ and $R_d$ are taken together to form a 3 to 10 membered heterocycle;

W is chosen from O, S or $NR_6$ wherein $R_6$ is chosen from H, $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl;

$R_1$ is chosen from $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl, $C_{1-12}$ alkyloxy, $C_{6-12}$ aryloxy or a halogen;

$R_2$ is chosen from $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl;

$R_3$ is chosen from $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl;

With the Proviso that:
i) when R1 is phenyl and Y is $COOCH_3$ then X is other than NH—$CH_2$-phenyl;
ii) when R1 is N-morpholino and Y is $COOCH_3$ then X is other than NH— (CO)-phenyl.

DETAILED DESCRIPTION OF THE INVENTION

In one embodiment, compounds of the present invention comprise those wherein the following embodiments are present, either independently or in combination.

In accordance with an other aspect of the present invention, there is provided a compound having the formula II:

$$\text{(II)}$$

or pharmaceutically acceptable salts thereof,
wherein each $R_1$, X and Y are as defined above.

In a further aspect, $R_1$ is chosen from $C_{6-12}$ aryl or $C_{3-10}$ heterocycle.

$R_1$ is $C_{3-6}$ heterocycle.

$R_1$ is chosen from thienyl, furanyl, pyridyl, oxazolyl, thiazolyl, pyrrolyl, benzofuranyl, indolyl, benzoxazolyl, benzothienyl, benzothiazolyl or quinolinyl.

$R_1$ is phenyl substituted by at least one substituent chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{1-12}$ alkyloxy, $C_{2-12}$ alkenyloxy, $C_{2-12}$ alkynyloxy, or $C_{6-12}$ aryloxy.

$R_1$ is phenyl substituted by one or two substituents chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{2-12}$ alkyloxy, $C_{2-12}$ alkenyloxy, $C_{2-12}$ alkynyloxy, or $C_{6-12}$ aryloxy.

$R_1$ is phenyl substituted by one or two substituents chosen from $C_{1-6}$ alkyl, $C_{2-6}$ alkenyl, $C_{2-6}$ alkynyl, $C_{3-10}$ heterocycle, halogen, nitro, amido, amino, amidino, guanido, CN, $COOC_{1-6}$ alkyl, $C_{1-12}$ alkyloxy, $C_{2-12}$ alkenyloxy, $C_{2-6}$-alkynyloxy, or $C_{6-12}$ aryloxy.

$R_1$ is phenyl substituted by one or two substituents chosen from $C_{1-12}$ alkyl, amino, halogen, nitro, amido, CN, $COOC_{1-12}$ alkyl, or $C_{1-12}$ alkyloxy.

$R_1$ is phenyl substituted by one or two substituents chosen from $C_{1-6}$ alkyl, amino, halogen, nitro, amido, CN, $COOC_{1-6}$ alkyl, or $C_{1-6}$ alkyloxy.

$R_1$ is phenyl.

In one embodiment, X is chosen from:

In a further embodiment, X is chosen from:

In yet a further aspect, X is:

In an other aspect, wherein X is

In further embodiments;

Y is chosen from $COOR_5$, tetrazole, CO-(amino acid) or $CONR_cR_d$.

Y is $COOR_5$.

$R_5$ is $C_{1-12}$ alkyl.

Y is CO-(amino acid).

Y is acid bio-isostere.

Y is a 5 membered heterocycle acid bio-isostere.

Y is tetrazole.

Y is $CONR_cR_d$.

Y is COOH.

In further embodiments;

$R_3$ is H or $C_{1-3}$ alkyl.

$R_3$ is $C_{1-3}$ alkyl.

$R_3$ is chosen from H, methyl, ethyl, n-propyl, isopropyl and cyclopropyl.

$R_3$ is chosen from methyl, ethyl, n-propyl, isopropyl and cyclopropyl $R_3$ is H.

In further embodiments;

$R_2$ is $C_{3-10}$ heterocycle.

$R_2$ is $C_{3-6}$ heterocycle.

$R_2$ is chosen from thienyl, furanyl, pyridyl, oxazolyl, thiazolyl, pyrrolyl, benzofuranyl, indolyl, benzoxazolyl, benzothienyl, benzothiazolyl or quinolinyl.

$R_2$ is $C_{1-12}$ alkyl.

$R_2$ is $C_{1-6}$ alkyl $R_2$ is chosen from cyclopentyl, cyclohexyl or t-butyl.

$R_2$ is $C_{6-12}$ aryl.

$R_2$ is chosen from indenyl, naphthyl or biphenyl.

$R_2$ is phenyl substituted by at least one substituent chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{1-12}$ alkyloxy, $C_{2-12}$ alkenyloxy, $C_{2-12}$ alkynyloxy, or $C_{6-12}$ aryloxy.

$R_2$ is phenyl substituted by one or two substituents chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{1-12}$ alkyloxy, $C_{2-12}$ alkenyloxy, $C_{2-12}$ alkynyloxy, or $C_{6-12}$ aryloxy.

$R_2$ is phenyl substituted by one or two substituents chosen from $C_{1-12}$ alkyl, amino, halogen, nitro, amido, CN, $COOC_{1-12}$ alkyl, or $C_{1-12}$ alkyloxy.

$R_2$ is phenyl substituted by one or two substituents chosen from $C_{1-6}$ alkyl, $C_{2-6}$ alkenyl, $C_{2-6}$ alkynyl, $C_{3-10}$ heterocycle, halogen, nitro, amido, amino, amidino, guanido, CN, COOC$_{1-6}$ alkyl, C$_{1-12}$ alkyloxy, C$_{2-12}$ alkenyloxy, C$_{2-12}$ alkynyloxy, or C$_{6-12}$ aryloxy.

R$_2$ is phenyl substituted by one or two substituents chosen from C$_{1-6}$ alkyl, amino, halogen, nitro, amido, CN, COOC$_{1-6}$ alkyl, or C$_{1-6}$ alkyloxy.

R$_2$ is methylphenyl.

R$_2$ is dichlorophenyl.

In one embodiment, the viral infection is chosen from Flavivirus infections.

In one embodiment, the Flavivirus infection is chosen from Hepatitis C virus (HCV), bovine viral diarrhea virus (BVDV), hog cholera virus, Dengue virus and yellow fever virus.

In another embodiment, the Flavivirus infection is Hepatitis C virus.

In one embodiment, there is also provided a method for inhibiting or reducing the activity of viral polymerase in a host comprising administering a therapeutically effective amount of a compound having the formula (I).

In another embodiment, the viral polymerase is Flaviridae viral polymerase.

In another embodiment, the viral polymerase is a RNA-dependant RNA polymerase.

In another embodiment, the viral polymerase is HCV polymerase.

It will be appreciated by those skilled in the art that the compounds of formula (I) can contain a chiral centre on the general formula (I). The compounds of formula (I) thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In accordance with the present invention, the compounds of formula (I) include:

Compound #1: 4-[Methyl-(4-methyl-benzoyl)-amino]-2-phenyl-thiazole-5-carboxylic acid;

Compound #2: 4-[(2,4-Dichloro-benzoyl)-methyl-amino]-2-phenyl-thiazole-5-carboxylic acid;

Compound #3: 4-[(2,4-Dichloro-benzoyl)-isopropyl-amino]-2-phenyl-thiazole-5-carboxylic acid;

Compound #4: 4-[(2,4-Dichloro-benzoyl)-ethyl-amino]-2-phenyl-thiazole-5-carboxylic acid;

Compound #5: 2-Phenyl-4-(toluene-2-sulfonylamino)-thiazole-5-carboxylic acid;

Compound #6: 4-[Isopropyl-(4-methyl-benzoyl)-amino]-2-phenyl-thiazole-5-carboxylic acid;

Compound #7: 4-(4-Chloro-benzoylamino)-2-phenyl-thiazole-5-carboxylic acid;

Compound #8: 4-(2,4-Dimethyl-benzoylamino)-2-phenyl-thiazole-5-carboxylic acid;

Compound #9: 4-(2,4-Dimethyl-benzenesulfonylamino)-2-phenyl-thiazole-5-carboxylic acid;

Compound #10: 2-Phenyl-4-(toluene-4-sulfonylamino)-thiazole-5-carboxylic acid;

Compound #11: 4-(2,4-Dichloro-benzoylamino)-2-phenyl-thiazole-5-carboxylic acid;

Compound #12: 4-(3-Methyl-benzoylamino)-2-phenyl-thiazole-5-carboxylic acid;

Compound #13: 4-[(2-Chloro-benzoyl)-methyl-amino]-2-phenyl-thiazole-5-carboxylic acid;

Compound #14: 4-[(4-Chloro-benzoyl)-methyl-amino]-2-phenyl-thiazole-5-carboxylic acid;

Compound #15: 4-[(4-Chloro-benzoylamino]-2-phenyl-thiazole-5-carboxylic acid; and Compound #16: 4-[(2,4-DIMETHYL-BENZOYL)-METHYL-AMINO]-2-MORPHOLIN-4-YL-THIAZOLE-5-CARBOXYLIC ACID.

Preferably, the compounds of the present invention are provided in the form of a single enantiomer at least 95%, more preferrably at least 97% and most preferably at least 99% free of the corresponding enantiomer.

More preferably the compound of the present invention are in the form of the (+) enantiomer at least 95% free of the corresponding (−) enantiomer.

More preferably the compound of the present invention are in the form of the (+) enantiomer at least 97% free of the corresponding (−) enantiomer.

More preferably the compound of the present invention are in the form of the (+) enantiomer at least 99% free of the corresponding (−) enantiomer.

In a more preferred embodiment, the compound of the present invention are in the form of the (−) enantiomer at least 95% free of the corresponding (+) enantiomer.

Most preferably the compound of the present invention are in the form of the (−) enantiomer at least 97% free of the corresponding (+) enantiomer.

More preferably the compound of the present invention are in the form of the (−) enantiomer at least 99% free of the corresponding (+) enantiomer.

There is also provided a pharmaceutically acceptable salts of the present invention. By the term pharmaceutically acceptable salts of compounds of general formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, citric, methanesulphonic, formic, benzoic, malonic, naphthalene-2-sulphonic, cysteic acid and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and NR$_4$+(where R is C$_{1-4}$ alkyl) salts.

References hereinafter to a compound according to the invention includes compounds of the general formula (I) and their pharmaceutically acceptable salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents an optionally substituted (by a halogen, nitro, SO$_3$R$_7$, PO$_3$R$_8$R$_9$, amido, COOH, cyano, C$_{1-6}$ alkyloxy, C$_{2-6}$ alkenyloxy, C$_{2-6}$ alkynyloxy, C$_{6-12}$ aryl, C$_{3-10}$ heterocycle, hydroxyl, amino, or COOQ, wherein Q is C$_{1-6}$ alkyl; C$_{2-6}$ alkenyl; C$_{2-6}$ alkynyl, C$_{6-12}$ aryl and R$_7$, R$_8$ and R$_9$ are chosen fromm H or C$_{1-6}$ alkyl) straight chain, branched chain or cyclic hydrocarbon moiety (e.g. isopropyl, ethyl, fluorohexyl or cyclopropyl). The term alkyl is also meant to include alkyls in which one or more hydrogen atoms is, replaced by an oxygen, (e.g. a benzoyl) or an halogen, more preferably, the halogen is fluoro (e.g. CF$_3$— or CF$_3$CH$_2$—).

The term "alkyloxy" represents an alkyl which is covalently bonded to the adjacent atom through an oxygen atom.

The terms "alkenyl" and "alkynyl" represent an alkyl containing at least one unsaturated group (e.g. allyl, acetylene, ethylene).

The term "amidino" represents —C(=NR$_{14}$)NR$_{15}$R$_{16}$ wherein R$_{14}$ R$_{15}$ and R$_{16}$ are C$_{1-6}$ alkyl, C$_{6-12}$ aryl or C$_{6-12}$ aralkyl, or R$_{15}$ and R$_{16}$ are taken together with the nitrogen to which they are attached to form a 3 to 10 membered heterocycle.

The term "guanidino" represents —NR$_{17}$C(=NR$_{18}$)NR$_{19}$R$_{20}$ wherein R$_{17}$, R$_{18}$, R$_{19}$ and R$_{20}$ are C$_{1-6}$ alkyl, C$_{6-12}$ aryl or C$_{6-12}$ aralkyl, or R$_{19}$ and R$_{20}$ are taken together with the nitrogen to which they are attached to form a 3 to 10 membered heterocycle.

The term "amido" represents —CONH$_2$, —CONHR$_{12}$ and —NR$_{12}$R$_{13}$ wherein R$_{12}$ and R$_{13}$ are C$_{1-6}$ alkyl, C$_{6-12}$ aryl or C$_{6-12}$ aralkyl, or R$_{12}$ and R$_{13}$ are taken together with the nitrogen to which they are attached to form a 3 to 10 membered heterocycle.

The term "amino" represents a derivative of ammonia obtained by substituting one or more hydrogen atom and include —NH$_2$, —NHR$_{10}$ and —NR$_{10}$R$_{11}$, wherein R$_{10}$ and R$_{11}$ are C$_{1-6}$ alkyl, C$_{6-12}$ aryl or C$_{6-12}$ aralkyl, or R$_{10}$ and R$_{11}$ are taken together with the nitrogen to which they are attached to form a 3 to 10 membered heterocycle.

The term "amino acid" represents all the essential and non-essential alpha amino acids, beta amino acids and derivatives (e.g. isoleucine, alanine, phenylglycine and beta-alanine).

The term "aryl" represents a carbocyclic moiety optionally substituted (by a halogen, nitro, SO$_3$R$_7$, PO$_3$R$_8$R$_9$, amido, COOH, cyano, C$_{1-6}$ alkyloxy, C$_{2-6}$ alkenyloxy, C$_{2-6}$ alkynyloxy, C$_{6-12}$ aryl, C$_{3-10}$ heterocycle, hydroxyl, amino, or COOQ, wherein Q is C$_{1-6}$ alkyl; C$_{2-6}$ alkenyl; C$_{2-6}$ alkynyl, C$_{6-12}$ aryl and R$_7$, R$_8$ and R$_9$ are chosen from H or C$_{1-6}$ alkyl) and containing at least one benzenoid-type ring (e.g., phenyl and naphthyl).

The term "aralkyl" represents an aryl group attached to the adjacent atom by a C$_{1-6}$ alkyl, C$_{2-6}$ alkenyl, or C$_{1-6}$ alkynyl (e.g. benzyl).

The term "aryloxy" represents an aryl which is covalently bonded to the adjacent atom through an oxygen atom.

Halogen are chosen from F, Cl, I, and Br.

The term "heterocycle" represents an optionally substituted (e.g. by a halogen, nitro, SO$_3$R$_7$, PO$_3$R$_8$R$_9$, amido, COOH, cyano, C$_{1-6}$ alkyloxy, C$_{2-6}$ alkenyloxy, C$_{2-6}$ alkynyloxy, C$_{6-12}$ aryl, C$_{3-10}$ heterocycle, hydroxyl, amino, or COOQ, wherein Q is C$_{1-6}$ alkyl; C$_{2-6}$ alkenyl; C$_{2-6}$ alkynyl, C$_{6-12}$ aryl and R$_7$, R$_8$ and R$_9$ are chosen from H or C$_{1-6}$ alkyl) saturated, partially saturated or unsaturated, cyclic moiety wherein said cyclic moeity is interrupted by at least one heteroatom (e.g. oxygen, sulfur or nitrogen). It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole; pyridine; pyrimidine; indole; piperidine; morpholine; thiophene and thiomorpholine.

The term "heteroaralkyl" represents an heterocycle group attached to the adjacent atom by a C$_{1-6}$ alkyl, C$_{1-6}$ alkenyl, or C$_{1-6}$ alkynyl(e.g.,thiophenyl).

When there is a sulfur atom present, the sulfur atom can be at different oxidation levels, ie. S, SO, or SO$_2$. The oxidation levels may also be represented by S(O) n wherein n is an integer between 0 and 2. All such oxidation levels are within the scope of the present invention.

The term "acid bio-isostere" refers to a moiety that is similar in physical and biological properties to an acid group. Non-limiting references describing acid bio-isosteres contemplated in accordance with the present invention include Lipinski et al, Quant. Struct. Act. Relat. 10, 109–117 (1991); Lipinski et al., Pestic. Sci., 29, 227–240 (1990); and LaVoie et al., Chem. Rev. 96, 3147–3176 (1996). Non limiting examples of acid bio-isostere include acidic 5 membered heterocycles such as tetrazole.

The term "independently" means that a substituent can be the same or different definition for each item.

As used in this application, the term "interferon" include: interferon likes molecules such as interferon (IFN), interferon α-2a, interferon α-2b, consensus interferon (CIFN), pegylated interferon (PEG-INTRON A,) interferon a-n1 (Wellferon), interferon alphacon-1 (Infergen), Rebetron (Intron A+Rebetol) and other types of interferons, engineered or purified interferon.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The compounds of the invention may also be used in combination with at least one additional agent chosen from antiviral agent, immunomodulating agent, antioxydant agent, antibacterial agent or antisense agent or other antiviral agents.

The compounds of the invention may also be used in combination with at least one additional agent chosen from HCV therapeutic vaccine or Hepatoprotector compound.

In one aspect of the invention, the compounds of the invention may be employed together with at least one other antiviral agent chosen from protease inhibitors, polymerase inhibitors, and helicase inhibitors.

In one aspect of the invention, the compounds of the invention may be employed together with at least one other antiviral agent chosen from interferon-$\alpha$, silybum marianum, interleukine-12, amantadine, ribozyme, ursodeoxycholic acid, hypericin, thymosin, N-acetyl cystein, ofloxacin, pentoxifylline, cyclosporin or ribavirin.

In another aspect of the invention, the compounds of the invention may be employed together with at least one other antiviral agent chosen from Interferon-$\alpha$, Ribavirin and Amantadine.

In one embodiment, the compounds of the invention may be employed together with at least one other antiviral agent chosen from Interferon-$\alpha$ and Ribavirin (REBETRON).

In one embodiment, the compounds of the invention may be employed together Interferon-$\alpha$.

In one embodiment, the compounds of the invention may be employed together with Ribavirin.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The entire disclosure of all applications, patents and publications, cited above and below, is hereby incorporated by reference.

The following general schemes and examples are provided to illustrate various embodiments of the present invention and shall not be considered as limiting in scope.

EXAMPLE 1

Preparation of 4-[Methyl-(4-methyl-benzoyl)-amino]-2-phenyl-thiazole-5-carboxylic acid (Compound #1).

SCHEME 1

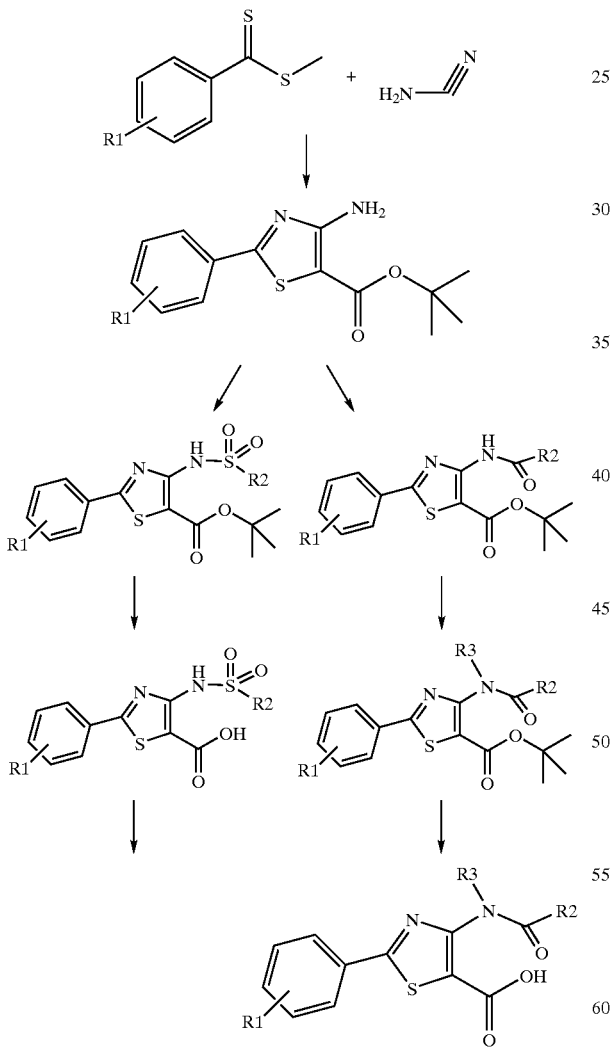

$R_1$ is a substituent (e.g. halogen, nitro, amidino, guanido, $CONH_2$, CN, COOR, alkyl, amino)
$R_2$ is a substituent (e.g. alkyl, aryl, heterocycle)
$R_3$ is a substituent (e.g. H, alkyl)

Step 1: Preparation of 4-Amino-2-phenyl-thiazole-5-carboxylic acid t-butyl ester.

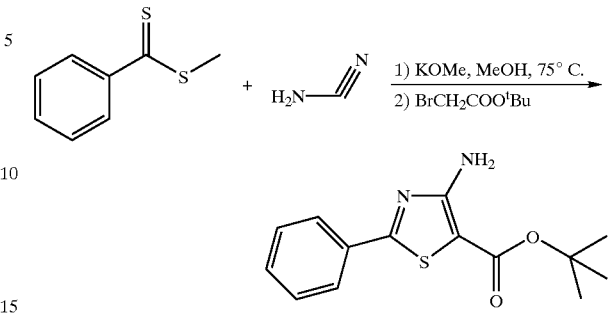

To a mixture of 1.6 g of dithiobenzoic acid methyl ester (see: H. D. Verkruijsse and L. Brandsma; *Journal of Organometallic Chemistry*, 332, 95 (1987)) and 420 mg of cyanoamide in 20 mL of anhydrous methanol was added 10 mL of 1M potassium methoxide in methanol. The mixture was heated at 70–75° C. for overnight, cooled to room temperature and then 2.3 g of 2-bromoacetate t-butyl ester was added slowly. The mixture was stirred for 4 h and a white solid was precipitated. At this point, 1.7 mL of triethyl amine was added and the mixture was stirred for overnight. The mixture was filtered. The filtrate was evaporated under reduced pressure. The residue was dissolved in methylene chloride, washed with water, brine solution. After drying over $MgSO_4$ solvent was removed on evaporator and the residue was purified on silica gel using hexane:EtOAc 95:5 and 9:1 as eluant to yiel 1.2 g of pure product as lightly yellow solid.

$^1$HNMR ($CDCl_3$, 400 MHz): δ in ppm: 7.93 (d, 2H, Ph), 7.45 (m, 3H, Ph), 5.81 (broad s, 2H, $NH_2$), 1.52 (s, 9H, t-butyl)

Step 2: Preparation of 4-(4-methyl-benzoylamino)-2-phenyl-thiazole-5-carboxylic acid t-butyl ester.

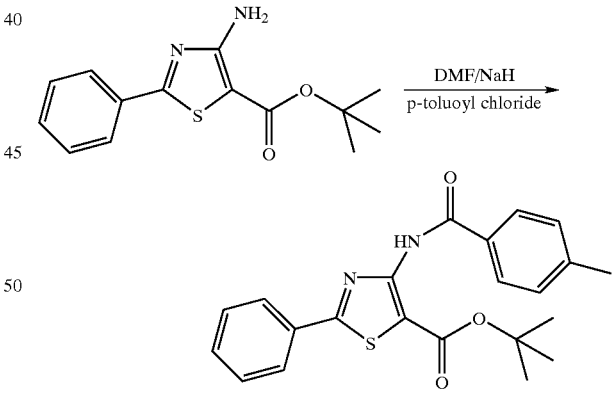

4-Amino-2-phenyl-thiazole-5-carboxylic acid t-butyl ester (78 mg) was dissolved in 3 mL of anhydrous DMF. NaH (45 mg, 60% dispersion in oil) was added. The solution turned to orange-red colour and stirred for 5 min. p-Toluoyl chloride (180 mg) in 1 mL of DMF was added. The mixture was stirred for overnight and poured into water. The aqueous solution was extracted with methylene chloride, washed with water and brine and dried over $MgSO_4$. Solvent was evaporated under reduced pressure. The residue was dissolved in 10 mL of methanol and treated with 1N aqueous lithium hydroxide (3 mL) for 2 h. Acetic acid was added to neutralized. Methanol was removed on an evaporator. The residue was dissolved with methylene chloride, washed with water and brine, dried over MgSO₄. Solvent was removed and residue was purified on silica gel using hexane:EtOAc 95:5, 9:1, 85:15 as eluant. It yielded 60 mg of pure compound.

¹HNMR (CDCl₃, 400 MHz): δ in ppm: 8.12 (d, 2H, Aromatic), 7.95 (d, 2H, Aromatic), 7.45 (m, 3H, Aromatic), 7.32 (d, 2H, Aromatic), 2.45 (s, 3H, —CH₃), 1.60 (s, 9H, t-butyl).

Step 3: Preparation of 4-[Methyl-(4-methyl-benzoyl)-amino]-2-phenyl-thiazole-5-carboxylic acid t-butyl ester

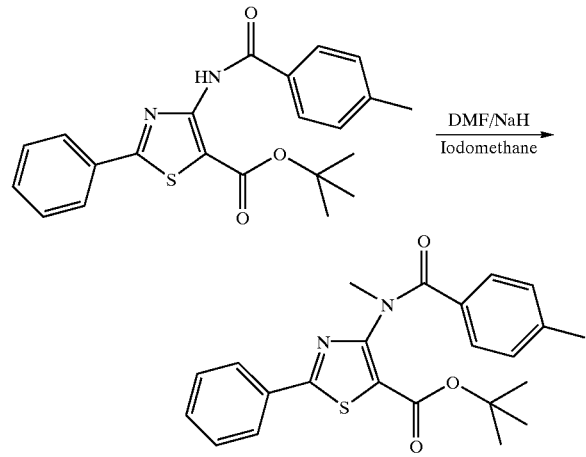

4-(4-methyl-benzoylamino)-2-phenyl-thiazole-5-carboxylic acid t-butyl ester (50 mg) was dissolved in anhydrous DMF (5 mL). NaH (16 mg, 60% dispersion oil) was added. The mixture was stirred for 10 min., followed by adding iodomethane (25 μL). Stirring was continued for overnight and poured into water. The aqueous solution was extracted with methylene chloride, washed with water, brine and dried over MgSO₄. Solvent was removed under reduced pressure. The residue was purified on silica gel using hexane:EtOAc 95:5. 9:1 and 85:5 as eluant. It yielded 25 mg of desired product.

¹HNMR (CDCl₃, 400 MHz): δ in ppm: 7.95 (d, 2H, Aromatic), 7.55 (m, 3H, Aromatic), 7.32 (d, 2H, Aromatic), 6.92 (d, 2H, Aromatic), 3.47 (s, 3H, —CH₃), 2.24 (s, 3H, —CH₃), 1.45 (s, 9H, t-butyl).

A second more polar product was also obtained (20 mg) and was identified as methyl ester derivative.

¹HNMR (CDCl₃, 400 MHz): δ in ppm: 7.95 (d, 2H, Aromatic), 7.55 (m, 3H, Aromatic), 7.28 (d, 2H, Aromatic), 7.05 (d, 2H, Aromatic), 3.75 (s, 3H, —CH₃), 3.47 (s, 3H, —CH₃), 2.24 (s, 3H, —CH₃

Step 4: Preparation of 4-[Methyl-(4-methyl-benzoyl)-amino]-2-phenyl-thiazole-5-carboxylic acid (Compound #1).

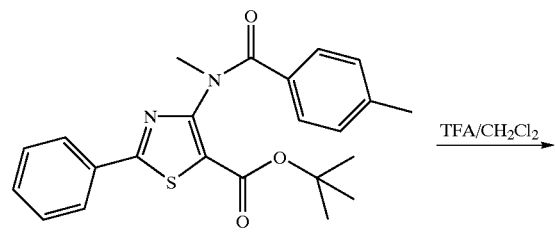

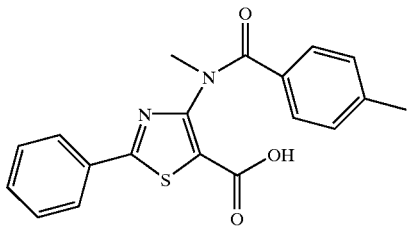

4-[Methyl-(4-methyl-benzoyl)-amino]-2-phenyl-thiazole-5-carboxylic acid t-butyl ester (23 mg) was dissolved in methylene chloride (3 mL) and trifluoroacetic acid (3 mL). Mixture stirred for overnight. Solvent was removed under reduced pressure. The residue was dissolved in methylene chloride and evaporated. The process was repeated three time. The residue was dissolved in methylene chloride and purified on silicagel (2 g silica gel cartridge) using Hexane:EtOAc 9:1, 4:1, 2:3 (10 mL each) as eluant.

It yielded 13 mg of desired product as a white foam.

¹HNMR (CDCl₃, 400 MHz): δ in ppm: 7.95 (d, 2H, Aromatic), 7.50 (m, 3H, Aromatic), 7.32 (d, 2H, Aromatic), 7.02 (d, 2H, Aromatic), 3.52 (s, 3H, —CH₃), 2.24 (s, 3H, —CH₃)

EXAMPLE 2

Preparation of 4-[(2,4-Dichloro-benzoyl)-methyl-amino]-2-phenyl-thiazole-5-carboxylic acid (Compound #2)

Step 1: Preparation of 4-(2,4-Dichloro-benzoylamino)-2-phenyl-thiazole-5-carboxylic acid t-butyl ester.

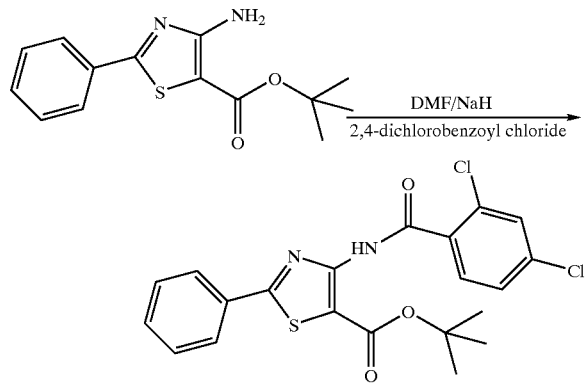

4-Amino-2-phenyl-thiazole-5-carboxylic acid t-butyl ester (217 mg was dissolved in 5 mL of anhydrous DMF. NaH (80 mg, 60% dispersion in oil) was added. The solution turned to orange-red colour and stirred for 5 min. 2,4-Dichlorobenzoyl chloride (0.22 mL) in 1 mL of DMF was added dropwise. The red colour was disappeared and mixture was stirred for 4 hrs and poured into water. The aqueous solution was extracted with methylene chloride, washed with water and brine and dried over MgSO₄. Solvent was evaporated under reduced pressure. The residue was dissolved in a solution of 1:2 methanol-THF (5 mL) and treated with 1N aqueous lithium hydroxide (3 mL) for 2 h. Acetic acid was added to neutralized. Methanol was removed on an evaporator. The residue was dissolved with methylene chloride, washed with water and brine, dried over MgSO₄. Solvent was removed and residue was purified on silica gel using hexane:EtOAc 95:5 as eluant. It yielded 155 mg of pure compound.

¹HNMR (CDCl₃, 400 MHz): δ in ppm: 10.35 (bs, 1H, NH), 7.85 (bs, 2H, Aromatic), 7.62 (d, 1H, Aromatic), 7.45 (m, 5H, Aromatic), 1.60 (s, 9H, t-butyl).

Step 2: Preparation of 4-[(2,4-Dichloro-benzoyl)-methyl-amino]-2-phenyl-thiazole-5-carboxylic acid t-butyl ester.

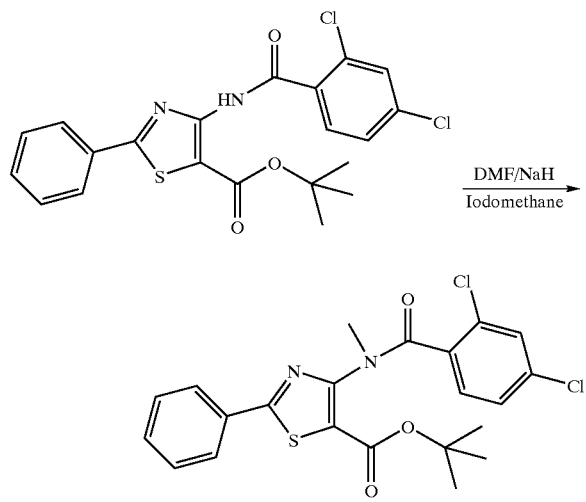

4-(2,4-Dichloro-benzoylamino)-2-phenyl-thiazole-5-carboxylic acid t-butyl ester (107 mg) was dissolved in anhydrous DMF (5 mL). NaH (20 mg, 60% dispersion oil) was added. A orange red colour appeared and the mixture was stirred for 5 min., followed by adding iodomethane (30 μL). The colour disappeared and stirring was continued for 1 h. The reaction was poured into water and acidified with acetic acid. The aqueous solution was extracted with methylene chloride, washed with water, brine and dried over MgSO₄. Solvent was removed under reduced pressure. The residue was purified on silica gel using hexane:EtOAc 95:5. 9:1 and 85:5 as eluent. It yielded 62 mg of desired product. There is the presence of a minor rotamer.

¹HNMR (CDCl₃, 400 MHz): δ in ppm: 7.80 (d, 2H, Aromatic), 7.47 (m, 3H, Aromatic), 7.32 (d, 2H, Aromatic), 7.20 (s, 1H, Aromatic), 7.05 (d, 2H, Aromatic), 3.47 (s, 3H, —CH₃), 1.55 (s, 9H, t-butyl)

Step 3: Preparation of 4-[(2,4-Dichloro-benzoyl)-methyl-amino]-2-phenyl-thiazole-5-carboxylic acid (Compound #2)

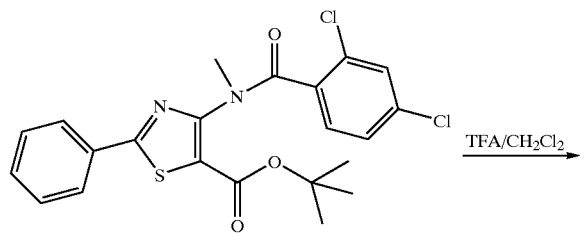

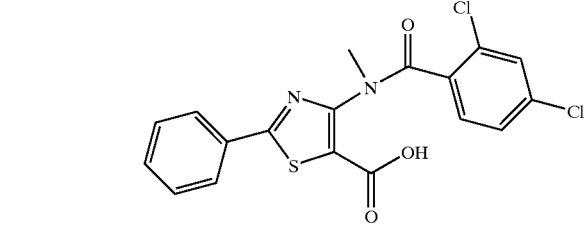

4-[(2,4-dichloro-benzoyl)-methyl-amino]-2-phenyl-thiazole-5-carboxylic acid t-butyl ester (60 mg) was dissolved in methylene chloride (3 mL) and trifluoroacetic acid (3 mL). Mixture stirred for overnight. Solvent was removed under reduced pressure. The residue was dissolved in methylene chloride and evaporated. The process was repeated three time. The residue was dissolved in methylene chloride and purified on silica gel (2 g silica gel cartridge) using Hexane:EtOAc 9:1, 4:1, 7:3, 1:1 and EtOAc (10 mL each) as eluant.

It yielded 32 mg of desired product as a white foam.

¹HNMR (CD₃OD, 400 MHz): δ in ppm: 7.82 (d, 2H, Aromatic), 7.50 (m, 3H, Aromatic), 7.37 (s, 1H, Aromatic), 730 (d, 2H, Aromatic), 7.20 (d, 2H, Aromatic), 3.52 (s, 3H, —CH₃).

The following compounds were prepared in a similar manner as described in examples 1 and 2:

Compound #3, Compound #4, Compound #13, Compound #14, Compound #7, Compound #8, Compound #11, Compound #12, Compound #7, Compound #8, Compound #11, and Compound #12)

Exemple 3

Preparation of 4-(2-methyl-benzensulfonylamino)-2-phenyl-thiazole-5-carboxylic acid (compound #5)

Step 1: Preparation of 4-(2-methyl-benzensulfonylamino)-2-phenyl-thiazole-5-carboxylic acid t-butyl ester.

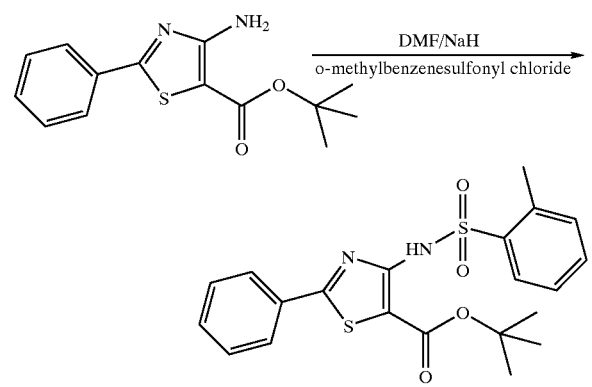

4-Amino-2-phenyl-thiazole-5-carboxylic acid t-butyl ester (100 mg was dissolved in 3 mL of anhydrous DMF. NaH (45 mg, 60% dispersion in oil) was added. The solution turned to orange-red colour and stirred for 5 min. o-Methylsulfonyl chloride (140 mg) in 1 mL of DMF was added dropwise. The mixture was stirred for overnight and poured into water. The aqueous solution was extracted with methylene chloride, washed with water and brine and dried over MgSO₄. Solvent was evaporated under reduced pressure. The residue was purified on silica gel using hexane:EtOAc 95:5, 9:1 as eluent. It yielded 40 mg of pure compound.

¹HNMR (CDCl₃, 400 MHz): δ in ppm: 9.60 (bs, 1H, NH), 8.40 (d, 1H, Aromatic), 7.78 (d, 2H, Aromatic), 7.45 (m, 4H, Aromatic), 7.28 (d, 2H, Aromatic), 2.70 (s, 3H, —CH₃), 1.60 (s, 9H, t-butyl)

Step 2: Preparation of 4-(2-methyl-benzensulfonylamino)-2-phenyl-thiazole-5-carboxylic acid (Compound #5)

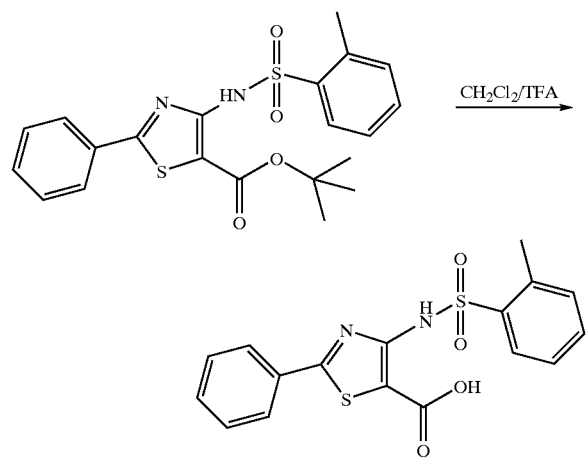

4-(2-methyl-benzensulfonylamino)-2-phenyl-thiazole-5-carboxylic acid t-butyl ester (40 mg) was dissolved in methylene chloride (3 mL) and trifluoroacetic acid (3 mL). Mixture stirred for overnight. Solvent was removed under reduced pressure. The residue was dissolved in methylene chloride and evaporated. The process was repeated three time. TLC indicated the presence of two product. The residue was dissolved in methylene chloride and purified on silica gel (2 g silica gel cartridge) using Hexane:EtOAc 9:1, 4:1, 7:3, 1:1 and EtOAc (10 mL each) as eluant.

It yielded 10 mg of the less polar product, which was identified as decarboxylated compound.

$^1$HNMR (CDCl$_3$, 400 MHz): δ in ppm: 7.95 (d, 1H, Aromatic), 7.70 (d, 2H, Aromatic), 7.50 (bs, 1H, Aromatic), 7.35 (m, 3H, Aromatic), 7.22 (d, 2H, Aromatic), 6.75 (s, 1H, Aromatic) 3.47 (s, 3H, —CH$_3$), 2.64 (s, 3H, —CH$_3$.

It yielded 17 mg of the polar product, which was identified as desired product as a white solid.

$^1$HNMR (DMSO$_{d6}$, 400 MHz): δ in ppm: 8.15 (d, 1H, Aromatic), 7.70 (d, 2H, Aromatic), 7.45 (m, 5H, Aromatic), 7.32 (d, 1H, Aromatic), 2.57 (s, 3H, CH3).

The following compounds were prepared in a similar manner as described in example 3:

Compound #9, Compound #10, Compound #15, Compound #16,

EXAMPLE 4

List of prepared compounds (Table 1)

The following compounds were prepared as listed in Table 1

TABLE I

List of compounds prepared having polymerase activity

| Compound # | Compound Name | Structure | RNA pol Assay1 IC$_{50}$ (μm)* |
|---|---|---|---|
| Compound #1 | 4-[Methyl-(4-methyl-benzoyl)-amino]-2-phenyl-thiazole-5-carboxylic acid | 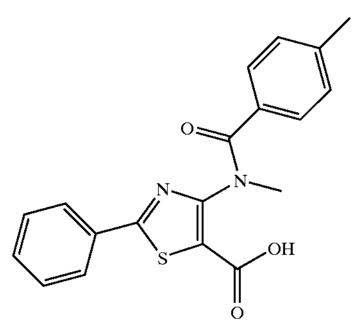 | +++ |
| Compound #2 | 4-[(2,4-Dichloro-benzoyl)-methyl-amino]-2-phenyl-thiazole-5-carboxylic acid | 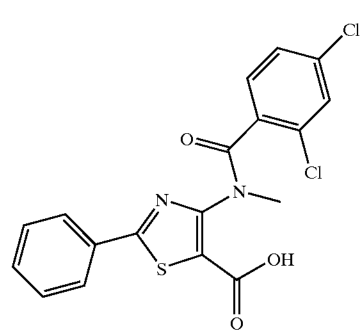 | +++ |

TABLE I-continued

List of compounds prepared having polymerase activity

| Compound # | Compound Name | Structure | RNA pol Assay1 IC$_{50}$ ($\mu$m)* |
|---|---|---|---|
| Compound #3 | 4-[(2,4-Dichloro-benzoyl)-isopropyl-amino]-2-phenyl-thiazole-5-carboxylic acid | 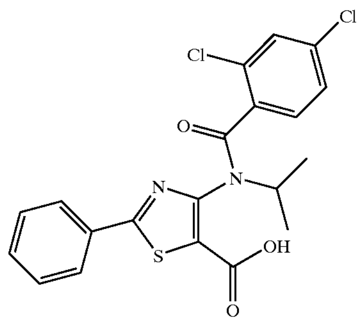 | +++ |
| Compound #4 | 4-[(2,4-Dichloro-benzoyl)-ethyl-amino]-2-phenyl-thiazole-5-carboxylic acid | 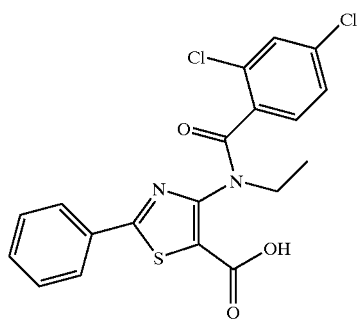 | +++ |
| Compound #5 | 2-Phenyl-4-(toluene-2-sulfonylamino)-thiazole-5-carboxylic acid | 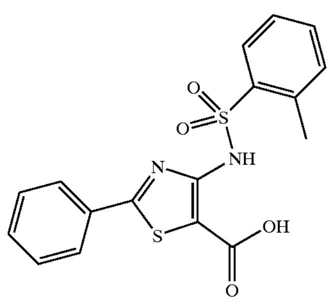 | ++ |
| Compound #6 | 4-[Isopropyl-(4-methyl-benzoyl)-amino]-2-phenyl-thiazole-5-carboxylic acid | 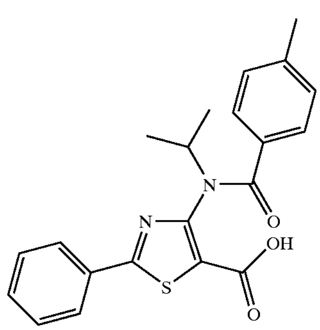 | +++ |

TABLE I-continued

List of compounds prepared having polymerase activity

| Compound # | Compound Name | Structure | RNA pol Assay1 IC$_{50}$ ($\mu$m)* |
|---|---|---|---|
| Compound #7 | 4-(4-Chloro-benzoylamino)-2-phenyl-thiazole-5-carboxylic acid | 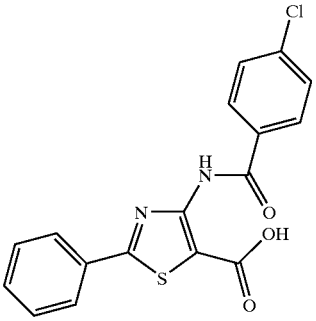 | + |
| Compound #8 | 4-(2,4-Dimethyl-benzoylamino)-2-phenyl-thiazole-5-carboxylic acid | 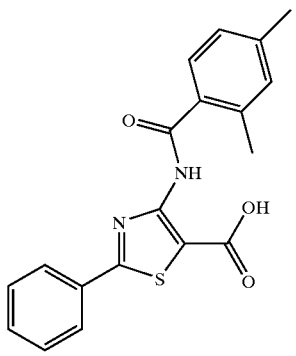 | + |
| Compound #9 | 4-(2,4-Dimethyl-benzenesulfonylamino)-2-phenyl-thiazole-5-carboxylic acid | 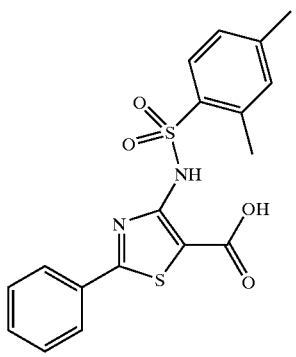 | ++ |
| Compound #10 | 2-Phenyl-4-(toluene-4-sulfonylamino)-thiazole-5-carboxylic acid | 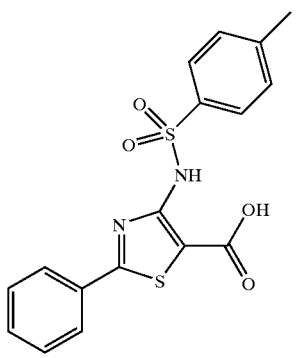 | + |

TABLE I-continued

List of compounds prepared having polymerase activity

| Compound # | Compound Name | Structure | RNA pol Assay1 IC$_{50}$ ($\mu$m)* |
|---|---|---|---|
| Compound #11 | 4-(2,4-Dichloro-benzoylamino)-2-phenyl-thiazole-5-carboxylic acid | 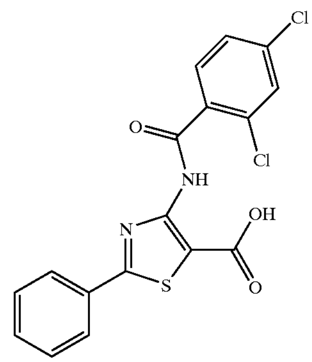 | ++ |
| Compound #12 | 4-(3-Methyl-benzoylamino)-2-phenyl-thiazole-5-carboxylic acid | 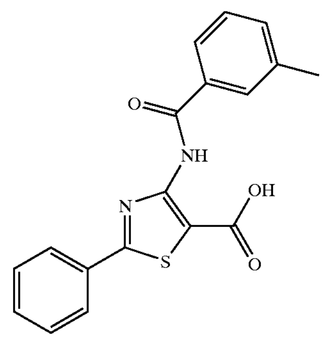 | + |
| Compound #13 | 4-[(2-Chloro-benzoyl)-methyl-amino]-2-phenyl-thiazole-5-carboxylic acid | 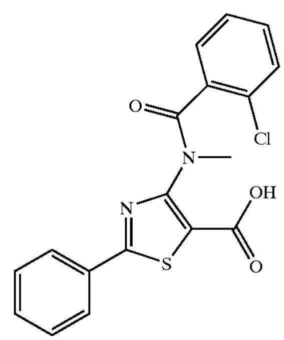 | ++ |
| Compound #14 | 4-[(4-Chloro-benzoyl)-methyl-amino]-2-phenyl-thiazole-5-carboxylic acid | 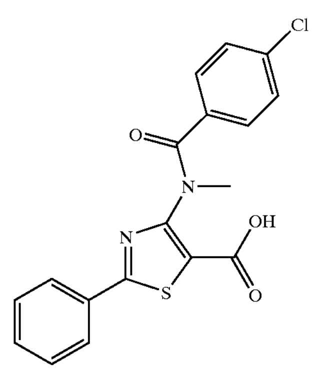 | +++ |

TABLE I-continued

List of compounds prepared having polymerase activity

| Compound # | Compound Name | Structure | RNA pol Assay1 IC$_{50}$ ($\mu$m)* |
|---|---|---|---|
| Compound #15 | 4-[(4-Chloro-benzoylamino]-2-phenyl-thiazole-5-carboxylic acid | 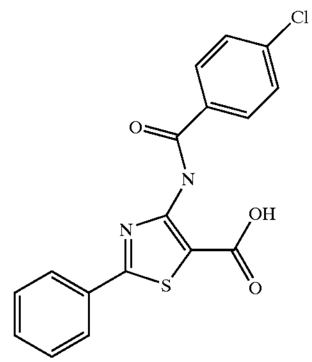 | ++ |
| Compound #16 | 4-[(2,4-DIMETHYL-BENZOYL)-METHYL-AMINO]-2-MORPHOLIN-4-YL-THIAZOLE-5-CARBOXYLIC ACID | 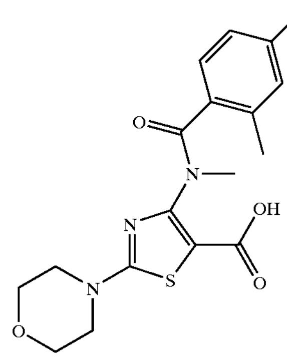 | ++ |

*+++ IC$_{50}$ < 5 $\mu$M
++ IC$_{50}$ 5 $\mu$M–20 $\mu$M
+ IC$_{50}$ > 20 $\mu$M

EXAMPLE 5

Evaluation of Compounds of Formula (I) in the HCV RNA-Dependent RNA Polymerase Assay The following references are all incorporated by reference:
1. Behrens, S., Tomei, L., De Francesco, R. (1996) *EMBO* 15, 12–22
2. Harlow, E, and Lane, D. (1988) *Antibodies: A Laboratory Manual.* Cold Spring Harbord Laboratory. Cold Spring Harbord. N.Y.
3. Lohmann, V., Körner, F., Herian, U., and Bartenschlager, R. (1997) *J. Virol.* 71, 8416–8428
4. Tomei, L., Failla, C., Santolini, E., De Francesco, R., and La Monica, N. (1993) *J Virol* 67, 4017–4026

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described below. Follows, are details of the RNA-dependent RNA polymerase assays used to test the compounds.

Expression of the HCV NS5B Protein in Insect Cells:

The cDNA encoding the entire NS5B protein of HCV-Bk strain, genotype 1b, was amplified by PCR using the primers NS5Nhe5' (5'-GCTAGCGCTAGCTCAATGTCCTACAC-ATGG-3') (SEQ ID NO: 1) and XhoNS53' (5'-CTCGAGCTCGAGCGTCCATCGGTTGGGGAG-3') (SEQ ID NO: 2) and the plasmid pCD 3.8–9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to 2CR-amplify the NS5B coding region, using the primers NS5B-H9 (5'-ATACATATGGCTAGCATGTCAATGTC-CTACACATGG-3') (SEQ ID NO: 3) and NS5B-R4 (5'-GGATCCGGATCCCGTTCATCGGTTGGGGAG-3') (SEQ ID NO: 4). NS5B-H9 spans a region of 15 nucleotides in the plasmid pET-21b followed by the translation initiation codon (ATG) and 8 nucleotides corresponding to the 5' end of the NS5B coding region (nt. 7590–7607 in the HCV sequence with the accession number M58335). NS5B-R4 contains two BamHI sites (underlined) followed by 18 nucleotides corresponding to the region around the stop codon in the HCV genome (nt. 9365–9347). The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 $\mu$g of pBac/NS5B, together with 1 $\mu$g of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a rabbit polyclonal antiserum (anti-NS5B) raised against a His-tagged version of the NS5B protein expressed in *E. coil*. Infections of Sf9 cells with this plaque purified virus were performed in one-liter spinner flasks at a cell density of $1.2 \times 10^6$ cells/ml and a multiplicity of infection of 5.

Preparation of a Soluble Recombinant NS5B Protein

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

Purification of Recombinant NS5B Using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In Vitro RNA-Dependent RNA Polymerase Assays Used to Evaluate Analogues:

RdRp assays were conducted using the homopolymeric template/primer polyA/oligo dT. All RdRp reactions were performed in a total volume of 50 ml, and in a basic buffer consisting of 20 mM Tris-HCl pH 7.5, 1 mM DTT, 50 mM NaCl, 5 mM $MgCl_2$, 0.5 $\mu$Ci $[\gamma^{32}P]$-UTp (3000 Ci/mmol), 15 $\mu$M cold UTP and 20 U RNasin (Promega). Standard HCV RdRp reactions contained 200 ng of purified NS5B protein. PolyA RNAs (Amersham-Pharmacia) was resuspended at 400 ng/ml. The primer oligodTl$_5$ (Canadian life technologies) was diluted to a concentration of 20 pmol/ml (7.6 ng/$\mu$l). Templates and primers were mixed volume to volume, denatured at 95° C. for 5 min and annealed at 37° C. for 10 min. Following a two hour incubation at 22° C., reactions were stopped by the addition of 100 $\mu$g of sonicated salmon sperm DNA (Life Technologies) and 1 ml of 10% trichloroacetic acid-0.5% tetrasodium pyrophosphate (TCA-PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac). Results are shown in Table 1, in the column indicated as Assay 1.

In Vitro HCV RdRp Flashplate Assay (Assay 2):

This assay consists on measuring the incorporation of $[^3H]$ radiolabelled UTP in a polyrA/biotinylated-oligo dT template-primer, captured on the surface of streptavidin-coated microtiter flashplates (NEN SMP 103A). In brief, a 400 ng/pl polyrA solution (Amersham Pharmacia Biotech) was mixed volume-to-volume with 5' biotin-oligo $dT_{12}$ at 20 pmol/$\mu$l. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded, compounds were added in a 10 $\mu$l solution followed by a 10 $\mu$l of a solution containing 100 mM $MgCl_2$, 200 mM Tris-HCl pH 7.5, 500 mM NaCl and 10 mM DTT. The enzymatic reaction was initiated upon addition of a 30 $\mu$l solution containing the enzyme and substrate to obtain the following concentrations: 25 $\mu$M UTP, 1 $\mu$Ci $[^3H]$ $\gamma$-UTP and 100 nM recombinant HCV NS5B. RdRp reactions were allowed to proceed for 2 hrs at room temperature after which wells were washed three times with a 0.15 M NaCl solution, air dried at 37 C, and counted in a Microbeta 1450 counter (Wallac). Results are shown in Table 1, in the column indicated as Assay 2.

What is claimed is:

1. A compound having the formula I:

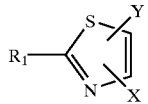
(I)

or a pharmaceutically acceptable salt thereof, wherein,

X is

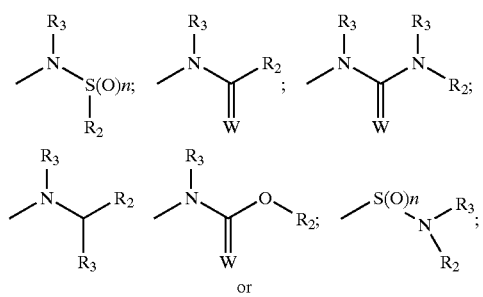

n is an integer between 0 and 2

Y is $COOR_5$, $COCOOR_5$, $P(O)OR_aOR_b$, $S(O)OR_5$, $S(O)_2OR_5$, an acid bio-isostere, CO-(amino acid), $CONR_cR_d$, $CON(R_4)$—$SO_2$—$R_5$ or $CONR_5OH$, $R_4$, $R_5$, $R_a$, $R_b$, $R_c$, and $R_d$ are each independently H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COGH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO_3R_8R_9$, amido COOH, cyano, $C_{1-6}$ alkyloxy, $C_{2-6}$ alkenyloxy, $C_{2-6}$ alkynyloxy, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

or $R_a$ and $R_b$ are taken together to form a 5 to 7 membered heterocycle;

or $R_c$ and $R_d$ are taken together to form a 3 to 10 membered heterocycle;

W is O, S or $NR_6$;

$R_6$ is H,
$C_{1-12}$ alkyl optionally substituted by halogen, nitro, $SO_3R_7$, $PO_3R_8R_9$, amido,
COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R7$, $PO_3R8R9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

$R_1$, is $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R1$, $PO3R_8R9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{1-12}$ alkyloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryloxy optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ or a halogen;

$R_2$ is $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

$R_3$ is H,
$C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

Q is $C_{1-6}$ alkyl, $C_{2-6}$ alkenyl, $C_{2-6}$ alkynyl, or $C_{6-12}$ aryl; and $R_7$, $R_8$ and $R_9$ are each independently H or $C_{1-6}$ alkyl;

With the provisos that:
when $R^1$ is phenyl and Y is $COOCH_3$ then X is other than NH—$CH_2$-phenyl; and
when $R^1$ N-morpholino and Y is $COOCH_3$ then X is other than NH—(CO)—phenyl.

2. A compound according to claim 1, wherein said compound is of formula II:

$$\text{(II)}$$

or is pharmaceutically acceptable salt thereof.

3. A compound as defined in claim 2, wherein $R_1$ is $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

4. A compound as defined in claim 2, wherein $R_1$ is $C_{3-6}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

5. A compound as defined in claim 2, wherein $R_1$ is thienyl, furanyl, pyridyl, oxazolyl, thiazolyl, pyrrolyl, benzofuranyl, indolyl, benzoxazolyl, benzothienyl, benzothiazolyl or quinolinyl.

6. A compound as defined in claim 2, wherein $R_1$ is phenyl substituted by at least one substituent chosen from $C_{1-12}$ alkyl, $C_{2-12}$ alkenyl, or $C_{2-12}$ alkynyl, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, halogen, nitro, amido, amino, amidino, guanido, CN, $COOC_{1-12}$ alkyl, $C_{1-12}$ alkyloxy, $C_{2-12}$ alkenyloxy, or $C_{2-12}$ alkynyloxy, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ beterocycle, hydroxyl, amino, or COOQ, and $C_{6-12}$ aryloxy optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

7. A compound as defined in claim 2, wherein $R_1$ is phenyl substituted by one or two substituents chosen from $C_{1-12}$ alkyl, $C_{2-12}$ alkenyl, or $C_{2-12}$ alkynyl, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, halogen, nitro, amido amino, amidino, guanido, CN, $COOC_{1-12}$ alkyl, $C_{1-12}$ alkyloxy, $C_{2-12}$ alkenyloxy, or $C_{2-12}$ alkynyloxy, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, and $C_{6-12}$ aryloxy optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

8. A compound as defined in claim 2, wherein $R_1$ is phenyl substituted by one or two substituents chosen from $C_{1-6}$ alkyl, $C_{2-6}$ alkenyl, or $C_{2-6}$ alkynyl, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ beterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, halogen, nitro, amido, amino, amidino, guanido, CN, $COOC_{1-6}$ alkyl, $C_{1-12}$ alkyloxy, $C_{2-12}$ alkenyloxy, or $C_{2-6}$ alkynyloxy, in each case optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, and $C_{6-12}$ aryloxy aryloxy optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

9. A compound as defined in claim 2, wherein $R_1$ is phenyl substituted by one or two substituents chosen from $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, amino, halogen, nitro, amido, CN, $COOC_{1-12}$ alkyl, or $C_{1-12}$ alkyloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

10. A compound as defined in claim 2, wherein $R_1$ is phenyl substituted by one or two substituents chosen from $C_{1-6}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, amino, halogen, nitro, amido, CN, $COOC_{1-6}$ alkyl, or $C_{1-6}$ alkyloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ.

11. A compound as defined in claim 2, wherein $R_1$ is phenyl.

12. A compound as defined in claim 2, wherein X is:

or

-continued

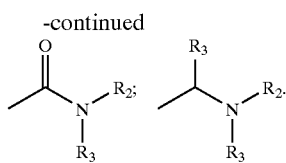

13. A compound as defined in claim 2, wherein X is:

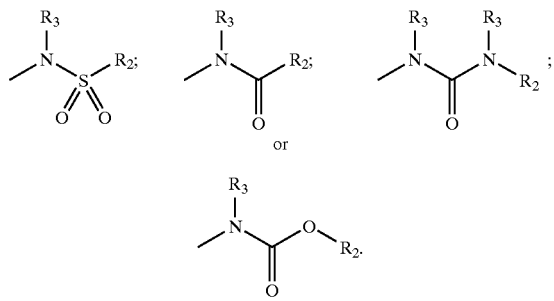

14. A compound as defined in claim 2, wherein X is:

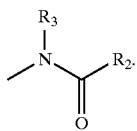

15. A compound as defined in claim 2, wherein X is

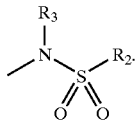

16. A compound as defined in claim 2, wherein Y is $COOR_5$, tetrazole, CO-(amino acid) or $CONR_cR_d$.
17. A compound as defined in claim 2, wherein Y is $COOR_5$.
18. A compound as defined in claim 15, wherein $R_5$ is $C_{1-12}$ alkyl.
19. A compound as defined in claim 2, wherein Y is CO-(amino acid).
20. A compound as defined in claim 2, wherein Y is tetrazole.
21. A compound as defined in claim 2, wherein Y is $CONR_cR_d$.
22. A compound as defined in claim 2, wherein Y is COOH.
23. A compound as defined in claim 2, wherein $R_3$ is H.
24. A compound as defined in claim 2, wherein $R_3$ is $C_{1-3}$ alkyl.
25. A compound as defined in claim 2, wherein $R_3$ is methyl, ethyl, n-propyl, isopropyl and cyclopropyl.
26. A compound as defined in claim 2, wherein $R_2$ is $C_{3-10}$ heterocycle.
27. A compound as defined in claim 2, wherein $R_2$ is $C_{3-6}$ heterocycle.
28. A compound as defined in claim 2, wherein $R_2$ is thienyl, furanyl, pyridyl, oxazolyl, thiazolyl, pyrrolyl, benzofuranyl, indolyl, benzoxazolyl, benzothienyl, benzothiazolyl or quinolinyl.
29. A compound as defined in claim 2, wherein $R_2$ is $C_{1-12}$ alkyl.
30. A compound as defined in claim 2, wherein $R_2$ is cyclopentyl, cyclohexyl or t-butyl.
31. A compound as defined in claim 2, wherein $R_2$ is $C_{6-12}$ aryl.
32. A compound as defined in claim 2, wherein $R_2$ is indenyl, naphthyl or biphenyl.
33. A compound as defined in claim 2, wherein $R_2$ is phenyl substituted by at least one substituent chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{1-12}$ alkyloxy, $C_{2-12}$ alkenyloxy, $C_{2-12}$ alkynyloxy, and $C_{6-12}$ aryloxy.
34. A compound as defined in claim 2, wherein $R_2$ is phenyl substituted by one or two substituents chosen from $C_{1-12}$ alkyl, $C_{2-12}$ alkenyl, $C_{2-12}$ alkynyl, $C_{3-10}$ heterocycle, halogen, nitro, amido, amino, amidino, guanido, CN, $COOC_{1-12}$ alkyl, $C_{1-12}$ alkyloxy, $C_{2-12}$ alkenyloxy, $C_{2-12}$ alkynyloxy, and $C_{6-12}$ aryloxy.
35. A compound as defined in claim 2, wherein $R_2$ is phenyl substituted by one or two substituents chosen from $C_{1-12}$ alkyl, amino, halogen, nitro, amido, CN, $COOC_{1-12}$ alkyl, and $C_{1-12}$ alkyloxy.
36. A compound as defined in claim 2, wherein $R_2$ is phenyl substituted by one or two substituents chosen from $C_{1-6}$ alkyl, $C_{2-6}$ alkenyl, $C_{2-6}$ alkynyl, $C_{3-10}$ heterocycle, halogen, nitro, amido, amino, amidino, guanido, CN, $COOC_{1-6}$ alkyl, $C_{1-12}$ alkyloxy, $C_{2-12}$ alkenyloxy, $C_{2-12}$ alkynyloxy, and $C_{6-12}$ aryloxy.
37. A compound as defined in claim 2, wherein $R_2$ is phenyl substituted by one or two substituents chosen from $C_{1-6}$ alkyl, amino, halogen, nitro, amido, CN, $COOC_{1-6}$ alkyl, and $C_{1-6}$ alkyloxy.
38. A compound as defined in claim 2, wherein $R_2$ is methylphenyl.
39. A compound as defined in claim 2, wherein $R_2$ is dichlorophenyl.
40. A compound as defined in claim 2, wherein $R_2$ is chlorophenyl.
41. A compound selected from the following:
   4-[Methyl-(4-methyl-benzoyl)-amino]-2-phenyl-thiazole-5-carboxylic acid;
   4-[(2,4-Dichloro-benzoyl)-methyl-amino]-2-phenyl-thiazole-5-carboxylic acid;
   4-[(2,4-Dichloro-benzoyl)-isopropyl-amino]-2-phenyl-thiazole-5-carboxylic acid;
   4-[(2,4-Dichloro-benzoyl)-ethyl-amino]-2-phenyl-thiazole-5-carboxylic acid;
   2-Phenyl-4-(toluene-2-sulfonylamino)-thiazole-5-carboxylic acid;
   4-[Isopropyl-(4-methyl-benzoyl)-amino]-2-phenyl-thiazole-5-carboxylic acid;
   4-(4-Chloro-benzoylamino)-2-phenyl--thiazole-5-carboxylic acid;
   4-(2,4-Dimethyl-benzoylamino)-2-phenyl-thiazole-5-carboxylic acid;
   4-(2,4-Dimethyl-benzenesulfonylamino)-2-phenyl-thiazole-5-carboxylic acid;
   2-Phenyl-4-(toluene-4-sulfonylamino)-thiazole-5-carboxylic acid;
   4-(2,4-Dichloro-benzoylamino)-2-phenyl-thiazole-5- carboxylic acid
   4-(3-Methyl-benzoylamino)-2-phenyl-thiazole-5- carboxylic acid4-[(2-Chloro-benzoyl)-methyl-amino]-2-phenyl-thiazole-5-carboxylic acid;
   4-[(4-Chloro-benzoyl)-methyl-amino]-2-phenyl-thiazole-5-carboxylic acid;

4-[(4-Chloro-benzoylamino]-2-phenyl-thiazole-5-carboxylic acid;

4-[(2,4-Dimethyl-benzoyl)-methyl-amino]-2-morpholin-4-yl-thiazole-5-cvarboxylic acid;

and pharmaceutical acceptable salts thereof.

42. A method for treating Flaviridae viral infection in a host comprising administering to the host a therapeutically effective amount of at least one compound according to claim 1.

43. A method according to claim 42, wherein said Flaviridae infection is hepatitis C (HCV).

44. A method for treating Flaviridae viral infection in a host comprising administering to the host a therapeutically effective amount of at least one compound according to claim 1 and at least one additional agent chosen from antiviral agent, immunomodulating agent, antioxydant agent, antibacterial agent or antisense agent.

45. A method according to claim 44, wherein said antiviral agent is chosen from a viral serine protease inhibitor, viral polymerase inhibitor and viral helicase inhibitor.

46. A method according to claim 44, wherein said additional agent is chosen from interferon-α, silybum marianum, interleukine-12, amantadine, ribozyme, ursodeoxycholic acid, hypericin, thymosin, N-acetyl cystein, ofloxacin, pentoxifylline, cyclosporin or ribavirin.

47. A method according to claim 44, wherein said additional agent is chosen from interferon-α or ribavirin.

48. A method according to in claim 44, wherein said Flaviridea infection is hepatitis C (HCV).

49. A pharmaceutical composition comprising at least one compound according to claim 1 together with at least one pharmaceutically acceptable carrier or excipient.

50. A compound according to claim 1, wherein $R_4$, $R_5$, $R_a$, $R_b$, $R_c$ and $R_d$ are each independently H, $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl;

or $R_a$ and $R_b$ are taken together to form a 5 to 7 membered heterocycle;

or $R_c$ and $R_d$ are taken together to form a 3 to 10 membered heterocycle;

W is O, S or $NR_6$;

$R_6$ is H, $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl;

$R_1$ is $C_{1-12}$ alkyl, $C_{2-12}$ alkenyl, $C_{2-12}$ alkynyl, $C_{6-12}$ aryl, $C_{3-10}$ heterocycle, $C_{3-10}$ heteroaralkyl, $C_{6-12}$ aralkyl, $C_{1-12}$ alkyloxy, $C_{6-12}$ aryloxy or a halogen;

$R_2$ is $C_{1-12}$ alkyl, $C_{2-12}$ alkenyl, $C_{2-12}$ alkynyl, $C_{6-12}$ aryl, $C_{3-10}$ heterocycle, $C_{6-12}$ aralkyl or $C_{3-10}$ heteroaralkyl; and $R_3$ is H, $C_{1-12}$ alkyl or $C_{6-12}$ aralkyl.

51. A compound according to claim 1, wherein Y is $COOR_5$, $COCOOR_5$, $P(O)OR_aOR_b$, $S(O)OR_5$, $S(O)_2OR_5$, $CONR_cR_d$, $CON(R_4)$—$SO_2$—$R_5$ or $CONR_5OH$.

52. A compound according to claim 1, wherein Y is $COOR_5$, $COCOOR_5$, $P(O)OR_aOR_b$, $S(O)OR_5$, $S(O)_2OR_5$, CO-(amino acid), $CONR_cR_d$, $CON(R_4)$—$SO_2$—$R_5$ or $CONR_5OH$, wherein the amino acid is selected from essential and non essential, alpha and beta, amino acids.

53. A compound according to claim 1, wherein Y is $COOR_5$, $COCOOR_5$, $P(O)OR_aOR_b$, $S(O)OR_5$, $S(O)_2OR_5$, CO-(amino acid), $CONR_cR_d$, $CON(R_4)$—$SO_2$—$R_5$ or $CONR_5OH$, wherein the amino acid is selected from isoleucine, alanine, phenylglycine and beta-alanine.

54. A compound according to claim 1, wherein

Y is $COOR_5$, $COCOOR_5$, or CO-(amino acid);

$R_5$ is H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R7$, $PO3R_8R9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, bydroxyl, amino, or COOQ, $C_{3-10}$ heteroaralkyl optionally substituted by a halogen, nitro, $SO_3R_7$, $PO3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R_7$, $PO3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

W is O, S or $NR_6$;

$R_6$ is H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

$R_1$ is $C_{1-12}$ alkyl optionally substituted by halogen, nitro, $SO_3R_7$, $PO3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{1-12}$ alkyloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or a halogen;

$R_2$ is $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

$R_3$ is H, $C_{1-12}$ alkyl optionally substituted by halogen, nitro, $SO_3R_7$, $PO_3R_8R9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, $C_{3-10}$ heterocycle, hydroxyl, amino, or COOQ;

Q is $C_{1-6}$ alkyl, $C_{2-6}$ alkenyl, $C_{2-6}$ alkynyl, or $C_{6-12}$ aryl; and $R_7$, $R_8$ and $R_9$ are each independently H or $C_{1-6}$ alkyl.

55. A method according to claim 42, wherein said Flaviridae infection is hepatitis C (HCV), bovine viral diarrhea virus (BVDV), hog cholera virus, Dengue virus or yellow fever virus.

56. A compound according to claim 1, wherein said compound is in the form of the (+) enantiomer at least 95% free of the corresponding (−) enantiomer.

57. A compound according to claim 1, wherein said compound is in the form of the (+) enantiomer at least 97% free of the corresponding (−) enantiomer.

58. A compound according to claim 1, wherein said compound is in the form of the (+) enantiomer at least 99% free of the corresponding (−) enantiomer.

59. A compound according to claim 1, wherein said compound is in the form of the (−) enantiomer at least 95% free of the corresponding (+) enantiomer.

60. A compound according to claim 1, wherein said compound is in the form of the (−) enantiomer at least 97% free of the corresponding (+) enantiomer.

61. A compound according to claim 1, wherein said compound is in the form of the (−) enantiomer at least 99% free of the corresponding (+) enantiomer.

62. A compound according to claim 1, wherein said compound is a pharmaceutically acceptable salt obtained from hydrochloric acid, hydrobromic acid, sulphuric acid, nitric acid, perchloric acid, fumaric acid, maleic acid, phosphoric acid, glycollic acid, lactic acid, salicylic acid, succinic acid, toleune-p-sulphonic acid, tartaric acid, acetic acid, citric acid, methanesulphonic acid, formic acid, benzoic acid, malonic acid, naphthalene-2-sulphonic acid, cysteic acid or benzenesulphonic acid.

63. A compound according to claim 1, wherein said compound is a pharmaceutically acceptable salt obtained from an alkali metal, an alkaline earth metal, ammonium or $NR_4+$, where R is $C_{1-4}$ alkyl.

64. A compound according to claim 54, wherein $R_5$ is H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkynyl optionally substituted by halogen, nitro, $SO_3R_7$, $PO_3R_8R9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{3-10}$ beterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ;

$R_6$ is H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{3-10}$ heterocycle optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{3-10}$ heteroaralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, or $C_{6-12}$ aralkyl optionally substituted by a halogen, nitro, $SO_3R_7$, $PO_3R_8R_9$, amido, COOR, cyano, $C_{1-6}$ alkyloxy, $C_{2-6}$ alkenyloxy, $C_{2-6}$ alkynyloxy, $C_{6-12}$ aryl, hydroxyl, amino, or COOQ;

$R_1$ is $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{1-12}$ alkyloxy optionally substituted by halogen, nitro, $SO_3R_7$, $PO_3R_8R_9$, amido, COGH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aryloxy optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, or a halogen;

$R_2$ is $C_{1-12}$ alkyl optionally substituted by halogen, nitro, $SO_3R_7$, $PO_3R_8R_9$, amido, COGH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkenyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{2-12}$ alkynyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, $C_{6-12}$ aryl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ; and $R_3$ is H, $C_{1-12}$ alkyl optionally substituted by halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ, or $C_{6-12}$ aralkyl optionally substituted by a halogen, nitro, $SO_3R_7$, $PO_3R_8R_9$, amido, COOH, cyano, $C_{1-6}$ alkyloxy, $C_{2-6}$ alkenyloxy, $C_{2-6}$ alkynyloxy, $C_{6-12}$ aryl, hydroxyl, amino, or COOQ.

65. A method for treating Flaviridae viral infection in a host comprising administering to the host a therapeutically effective amount of at least one compound according to claim 54.

66. A method according to claim 65, wherein said Flaviridae infection is hepatitis C (HCV).

67. A method for treating Flaviridae viral infection in a host comprising administering to the host a therapeutically effective amount of at least one compound according to claim 54 and at least one additional agent chosen from antiviral agent, immunomodulating agent, antioxydant agent, antibacterial agent or antisense agent.

68. A method according to claim 67, wherein said antiviral agent is chosen from a viral serine protease inhibitor, viral polymerase inhibitor and viral helicase inhibitor.

69. A method according to claim 67, wherein said additional agent is chosen from interferon-α, silybum marianum, interleukine- 12, amantadine, ribozyme, ursodeoxycholic acid, hypericin, thymosin, N-acetyl cystein, ofloxacin, pentoxifylline, cyclosporin or ribavirin.

70. A method according to claim 67, wherein said additional agent is chosen from interferon-α or ribavirin.

71. A method as defined in claim 67, wherein said Flaviridea infection is hepatitis C (HCV).

72. A method for treating Flaviridae viral infection in a host comprising administering to the host a therapeutically effective amount of at least one compound according to claim 64.

73. A method according to claim 72, wherein said Flaviridae infection is hepatitis C (HCV).

74. A method for treating Flaviridae viral infection in a host comprising administering to the host a therapeutically effective amount of at least one compound according to claim 64 and at least one additional agent chosen from antiviral agent, immunomodulating agent, antioxydant agent, antibacterial agent or antisense agent.

75. A method according to claim 74, wherein said antiviral agent is chosen from a viral serine protease inhibitor, viral polymerase inhibitor and viral helicase inhibitor.

76. A method according to claim 74, wherein said additional agent is chosen from interferon-α, silybum marianum, interleukine- 12, amantadine, ribozyme, ursodeoxycholic acid, hypericin, thymosin, N-acetyl cystein, ofloxacin, pentoxifylline, cyclosporin or ribavirin.

77. A method according to claim 74, wherein said additional agent is chosen from interferon-α or ribavirin.

78. A method as defined in claim 74, wherein said Flaviridea infection is hepatitis C (HCV).

\* \* \* \* \*

UNITED STATES PATENT AND TRADEMARK OFFICE
CERTIFICATE OF CORRECTION

PATENT NO. : 6,936,629 B2  Page 1 of 1
APPLICATION NO. : 10/324140
DATED : August 30, 2005
INVENTOR(S) : Chan Chung Kong et al.

It is certified that error appears in the above-identified patent and that said Letters Patent is hereby corrected as shown below:

On first page, Attorney, Agent or Firm reads "Miller, White, Zdano, Branigan, P.C." should read -- Millen, White, Zelano & Branigan, P.C. --
Column 30, line 61 reads "COGH" should read -- COOH --
Column 31, line 47 reads "$SO_3R_7$, $PO_3R8R9$" should read -- $SO_3R_7$, $PO_3R_8R_9$ --
Column 31, line 63 reads "$SO_3R1$, $PO3R_8R9$" should read -- $SO_3R_7$, $PO_3R_8R_9$ --
Column 32, line 38 reads "$SO_3R7$" should read -- $SO_3R_7$ --
Column 32, line 66 "when $R^1$ N-morpholino" should read -- when $R^1$ N-morpholino --
Column 33, line 47 reads "beterocycle" should read -- heterocycle --
Column 34, line 15 reads "beterocycle" should read -- heterocycle --
Column 34, line 27 reads "aryloxy aryloxy" should read -- aryloxy --
Column 37, line 4 reads "cvarboxylic" should read -- carboxylic --
Column 38, line 9 reads "$SO_3R7$, $PO3R_8R9$" should read -- $SO_3R_7$, $PO_3R_8R_9$ --
Column 38, line 24 reads "bydroxy" should read -- hydroxyl --
Column 38, line 26 reads "$PO3R_8R_9$" should read -- $PO_3R_8R_9$ --
Column 38, line 30 reads "$PO3R_8R_9$" should read -- $PO_3R_8R_9$ --
Column 38, line 65 reads "$PO3R_8R_9$" should read -- $PO_3R_8R_9$ --
Column 39, line 10 reads "$PO3R_8R_9$" should read -- $PO_3R_8R_9$ --
Column 40, line 48 reads "beterocycle" should read -- heterocycle --
Column 41, line 21 reads "COOR" should read -- COOH --
Column 41, line 45 reads "COGH" should read -- COOH --
Column 41, line 55 reads "COGH" should read -- COOH --

Signed and Sealed this

Sixth Day of February, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence

```
<220> FEATURE:
<223> OTHER INFORMATION: Description of Artificial Sequence: Primer

<400> SEQUENCE: 1
gctagcgcta gctcaatgtc ctacacatgg                                      30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ctcgagctcg agcgtccatc ggttggggag                                      30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 3
atacatatgg ctagcatgtc aatgtcctac acatgg                               36

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ggatccggat cccgttcatc ggttggggag                                      30
```